United States Patent
Han et al.

(10) Patent No.: US 8,938,087 B2
(45) Date of Patent: Jan. 20, 2015

(54) METHOD AND APPARATUS FOR PROCESSING IMAGE AND MEDICAL IMAGE SYSTEM PERFORMING THE METHOD

(75) Inventors: Seok-min Han, Seongnam-si (KR); Dong-goo Kang, Suwon-si (KR); Young-hun Sung, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 719 days.

(21) Appl. No.: 13/221,322

(22) Filed: Aug. 30, 2011

(65) Prior Publication Data

US 2012/0101733 A1   Apr. 26, 2012

(30) Foreign Application Priority Data

Oct. 21, 2010   (KR) ................. 10-2010-0103056

(51) Int. Cl.
| | |
|---|---|
| G06K 9/00 | (2006.01) |
| G06T 5/50 | (2006.01) |
| G06T 7/00 | (2006.01) |
| G06T 5/00 | (2006.01) |
| A61B 6/00 | (2006.01) |

(52) U.S. Cl.
CPC ................. G06T 5/50 (2013.01); G06T 7/0012 (2013.01); G06T 5/005 (2013.01); G06T 2207/10116 (2013.01); G06T 2207/30068 (2013.01)
USPC ............................ 382/100; 382/274; 600/476

(58) Field of Classification Search
USPC ......... 382/100, 103, 106–107, 128, 134, 162, 382/168, 172–173, 181, 194, 232, 254, 258, 382/274, 276, 291, 305, 312; 600/476; 378/20, 21, 53, 5
See application file for complete search history.

(56) References Cited

U.S. PATENT DOCUMENTS

| | | | |
|---|---|---|---|
| 6,173,034 B1 | 1/2001 | Chao | |
| 6,674,835 B2 * | 1/2004 | Kaufhold et al. | 378/53 |
| 7,873,198 B2 * | 1/2011 | Shepherd et al. | 382/132 |
| 2004/0264627 A1 * | 12/2004 | Besson | 378/5 |
| 2005/0187478 A1 * | 8/2005 | Beaudry et al. | 600/476 |
| 2010/0034348 A1 * | 2/2010 | Yu | 378/20 |
| 2010/0046814 A1 | 2/2010 | Dewaele et al. | |

FOREIGN PATENT DOCUMENTS

JP    2007-268275    10/2007

* cited by examiner

*Primary Examiner* — Seyed Azarian
(74) *Attorney, Agent, or Firm* — NSIP Law

(57) ABSTRACT

An image processing apparatus is provided. The image processing apparatus includes an image mapping unit for generating a mapping image in which first radiation images of multi-energy bands with respect to a local region of a body are mapped to a second radiation image with respect to a thickness variable phantom, an image analyzing unit for analyzing a reference region corresponding to normal tissue in the local region and a peculiar region corresponding to abnormal tissue in the local region based on the mapping image, and an enhancement image generating unit for generating a tissue enhancement image that has a shape of the local region in the first radiation images and enhances regions of pixel positions, that are mapped to the peculiar region, of the first radiation images.

25 Claims, 7 Drawing Sheets

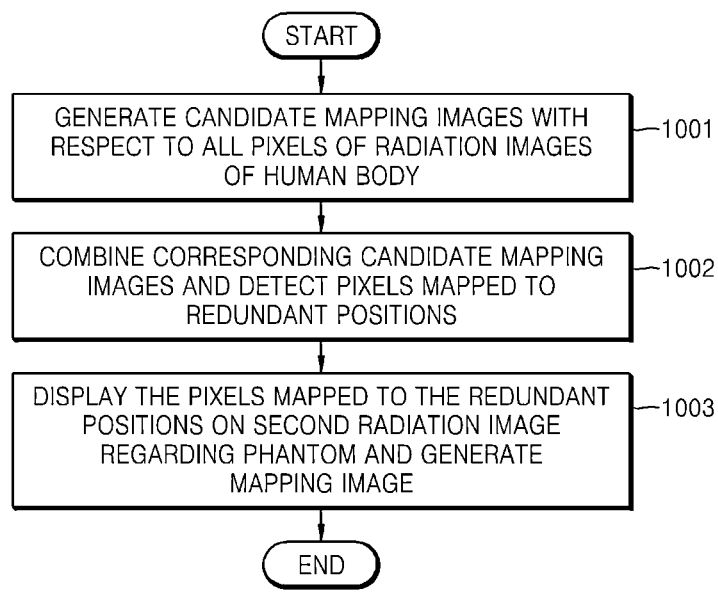

METHOD AND APPARATUS FOR PROCESSING IMAGE AND MEDICAL IMAGE SYSTEM PERFORMING THE METHOD

CROSS-REFERENCE TO RELATED APPLICATIONS

This application claims the benefit under 35 U.S.C. §119(a) of Korean Patent Application No. 10-2010-0103056, filed on Oct. 21, 2010, in the Korean Intellectual Property Office, the entire disclosure of which is incorporated herein by reference for all purposes.

BACKGROUND

1. Field

The following disclosure relates to a method and apparatus for processing an image, and a medical image system performing the method.

2. Description of the Related Art

A medical image system that uses radiation, for example X-rays, may obtain a radiation image projected by irradiating X-rays onto a subject, such as, for example, a human body. The amount of X-rays absorbed by an irradiation material may depend on a type and density of the irradiation material or on an X-ray energy band. For example, an X-ray attenuation coefficient of bone may be much higher than that of soft tissue. Thus, since a contrast between the bone and the soft tissue may be high in the radiation image, the soft tissue and the bone of the radiation image may be clearly identified. However, since different tissues included in the soft tissue may have similar X-ray attenuation coefficients of a single energy band, the tissues may have similar intensities in the radiation image. Thus, it may be difficult to identify different tissues included in the soft tissue of the radiation image.

SUMMARY

Provided are methods and apparatuses for processing an image by enhancing an abnormal tissue identified from normal tissue, and a medical image system performing the methods. Provided are computer readable recording media storing programs for executing the methods.

In one general aspect, an image processing apparatus is provided. The image processing apparatus includes an image mapping unit for generating a mapping image in which first radiation images of multi-energy bands with respect to a local region of a body are mapped to a second radiation image with respect to a thickness variable phantom, an image analyzing unit for analyzing a reference region corresponding to normal tissue in the local region and a peculiar region corresponding to abnormal tissue in the local region based on the mapping image, and an enhancement image generating unit for generating a tissue enhancement image that has a shape of the local region in the first radiation images and enhances regions of pixel positions, that are mapped to the peculiar region, of the first radiation images.

The image mapping unit may map pixels of the same positions of the first radiation images to the second radiation image.

The image mapping unit may generate the mapping image by detecting pixels mapped to redundant positions of the second radiation image from a result obtained by mapping the pixels of the same positions of the first radiation images to the second radiation image.

The image mapping unit may include a candidate mapping image generating unit for mapping pixels of the same positions of the first radiation images to the second radiation image, and generating corresponding candidate mapping images, a mapping pixel detecting unit for combining the corresponding candidate mapping images and detecting pixels mapped to redundant positions, and a mapping image generating unit for displaying the pixels mapped to the redundant positions on the second radiation image and generating a mapping image.

A position of the reference region of the mapping image may indicate a thickness of the normal tissue, and a position of the peculiar region thereof may indicate a thickness of the local region including the abnormal tissue.

The image analyzing unit may include a reference region estimating unit for estimating the position of the reference region in the mapping image, and a peculiar region determining unit for determining at least one peculiar region separate from the reference region in the mapping image.

The peculiar region determining unit may determine a mapped pixel separate from the reference region by a distance that is greater than a threshold in the mapping image as the at least one peculiar region.

The reference region estimating unit may estimate the reference region based on a distribution of pixels mapped to the mapping image.

The image processing apparatus may further include a tissue characteristics estimating unit for estimating a thickness and density of a local region based on a shape and position of the analyzed reference region in the mapping image, and identifying an abnormal tissue type based on a shape and a position of the analyzed peculiar region.

The first radiation images may include one first radiation image from a first energy band of the multi-energy bands and another first radiation image from a second energy band of the multi-energy bands. The first energy band may have a different energy than the second energy band.

In another general aspect, an image processing method is provided. The image processing method includes generating a mapping image in which first radiation images of multi-energy bands with respect to a local region of a body are mapped to a second radiation image with respect to a thickness variable phantom, analyzing a reference region corresponding to normal tissue in the local region and a peculiar region corresponding to abnormal tissue in the local region based on the mapping image, and generating a tissue enhancement image that has a shape of the local region in the first radiation images and enhances regions of pixel positions, that are mapped to the peculiar region, of the first radiation images.

The generating of the mapping image may include mapping pixels of the same positions of the first radiation images to the second radiation image.

The generating of the mapping image may include generating the mapping image by detecting pixels mapped to redundant positions of the second radiation image from a result obtained by mapping the pixels of the same positions of the first radiation images to the second radiation image.

The generating of the mapping image may include mapping pixels of the same positions of the first radiation images to the second radiation image, and generating corresponding candidate mapping images, combining the corresponding candidate mapping images and detecting pixels mapped to redundant positions, and displaying the pixels mapped to the redundant positions on the second radiation image and generating a mapping image.

The analyzing may include estimating the position of the reference region in the mapping image, and determining at least one peculiar region separate from the reference region in the mapping image.

The determining of the peculiar region may include determining a mapped pixel separate from the reference region by a distance that is greater than a threshold in the mapping image as the at least one peculiar region.

The image processing apparatus may further include estimating a thickness and density of a local region based on a shape and position of the analyzed reference region in the mapping image, and identifying a type of an abnormal tissue based on a shape and a position of the analyzed peculiar region.

A computer readable recording medium storing a program for executing the method.

The first radiation images may include one first radiation image from a first energy band of the multi-energy bands and another first radiation image from a second energy band of the multi-energy bands. The first energy band may have a different energy than the second energy band.

In yet another general aspect, a medical image system is provided. The medical image system includes a radiation image photographing unit for irradiating radiation onto a local region of a body and a thickness variable phantom, and obtaining first radiation images of multi-energy bands of the local region of the body and a second radiation image of the thickness variable phantom, an image processing apparatus for generating a mapping image in which the first radiation images are mapped to the second radiation image, analyzing a reference region corresponding to normal tissue in the local region and a peculiar region corresponding to abnormal tissue in the local region based on the mapping image, and generating a tissue enhancement image that has a shape of the local region in the first radiation images and enhances regions of pixel positions, that are mapped to the peculiar region of the first radiation images, and a display unit for displaying the tissue enhancement image.

The image processing apparatus maps pixels of the same positions of the first radiation images to the second radiation image, detects pixels mapped to redundant positions of the second radiation image from a result obtained by mapping the pixels of the same positions of the first radiation images to the second radiation image, and generates the mapping image.

The image processing apparatus may determine a mapped pixel separate from the reference region by a distance that is greater than a threshold in the mapping image as the at least one peculiar region.

The first radiation images may include one first radiation image from a first energy band of the multi-energy bands and another first radiation image from a second energy band of the multi-energy bands. The first energy band may have a different energy than the second energy band.

In yet another general aspect, An image processing method is provided. The image processing method includes generating a plurality of first radiation images corresponding to a plurality of energy bands with respect to a local region of a body and a second radiation image with respect to a thickness variable phantom, detecting a pixel of a redundant position based on the first radiation images and second radiation image, and enhancing regions of pixel positions, that are mapped to a peculiar region corresponding to abnormal tissue in the local region of the first radiation images based on the detecting operation.

The first radiation images may include one first radiation image from a first energy band and another radiation image from a second energy band. The first energy band may have a different energy than the second energy band.

Other features and aspects may be apparent from the following detailed description, the drawings, and the claims.

BRIEF DESCRIPTION OF THE DRAWINGS

FIG. 10 is a flowchart illustrating an operation of FIG. 9 of generating a mapping image.

Figure 1:
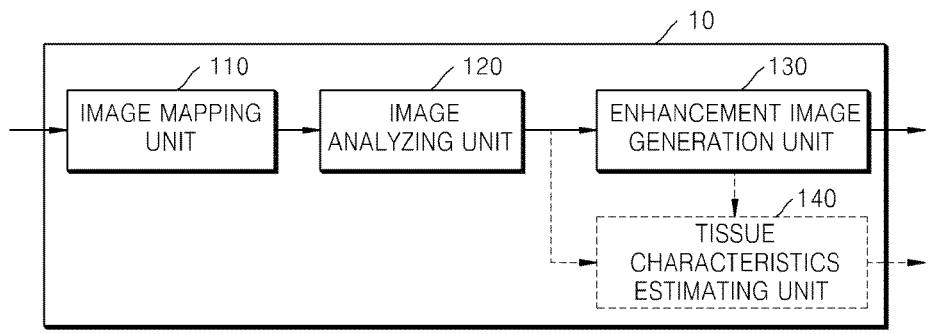
FIG. 1 is a block diagram illustrating an image processing apparatus, based on an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 illustrates an image processing apparatus 10, based on an example embodiment. Referring to FIG. 1, the image processing apparatus 10 includes an image mapping unit 110, an image analyzing unit 120, and an enhancement image generation unit 130.

The image processing apparatus 10 of FIG. 1 includes elements related to the example embodiment. In addition, general-use elements may be further included in the image processing apparatus 10 of FIG. 1.

Furthermore, the image mapping unit 110, an image analyzing unit 120, and an enhancement image generation unit 130 of the image processing apparatus 10 may be implemented as a processor or a plurality of processors. The processor may include, for example, an array of logic gates, or a combination of a general-use microprocessor and a memory in which a program to be executed in the general-use microprocessor is stored. In addition, it is understood that the processor may be implemented by using a different type of hardware.

The image processing apparatus 10 of the example embodiment may perform predetermined processing on an irradiation image obtained by irradiating radiation onto a local region of a human body. In this regard, although the local region of the human body of the example embodiment is breast tissue, the example embodiment is not limited to breast tissue.

With regard to the irradiation image, for example, an X-ray image, the relationship between an incident intensity and a transmitted intensity will be described. X-ray transmittance may depend on a type and density of a subject and an X-ray energy band. The incident intensity and the transmitted intensity may be expressed based on equation 1 below, $$I(E) = I_0(E)e^{-\mu(E)\rho x} \qquad \text{[Equation 1]}$$

where, $I(E)$ corresponds with the transmitted intensity, $I_0(E)$ corresponds with the incident intensity, $\mu(E)$ corresponds with a mass attenuation coefficient, $\rho$ corresponds with the density of the subject, and x corresponds with a thickness of the subject. This principle is known as the Beer-Lambert Law.

In general, the X-ray attenuation coefficient differs based on types of penetrated materials and X-ray energy bands. For example, X-ray attenuation coefficients may include adipose tissue, glandular tissue, infiltrating ductal carcinoma (IDC), etc. based on X-ray energy bands.

When radiation having two or more multi-energy bands is used, images I1, I2, ..., In (where n is the energy band) for respective energy bands may be expressed based on equation 2 below, $$\begin{pmatrix} I_1 \\ I_2 \\ \vdots \\ I_N \end{pmatrix} = \begin{pmatrix} \int_E w_1(E)\left(\exp\left(-\sum_i C_i\mu_i(E)\right)\right)dE \\ \int_E w_2(E)\left(\exp\left(-\sum_i C_i\mu_i(E)\right)\right)dE \\ \vdots \\ \int_E w_N(E)\left(\exp\left(-\sum_i C_i\mu_i(E)\right)\right)dE \end{pmatrix} \qquad \text{[Equation 2]}$$

Where, $W_N$ corresponds with an X-ray incident intensity of the energy band n, $$C_i = \int_L c_i(r)dr,$$

corresponds with a material density projection Ci of each position vector r. When the images I1, I2, ..., In (where n is the energy band) for respective energy bands may be obtained in equation 2, the material density projection Ci may be obtained from each of the images I1, I2, ..., In for respective energy bands. Thus, tissue types of the local region tissue of the human body may be identified.

A number of attenuation basis of the tissue types of the local region tissue of the human body may be 2. The attenuation basis may include photoelectric absorption and Compton scattering. Thus the two tissue types may be identified.

One of the reasons why the radiation of multi-energy bands is used in the example embodiment is as follows. A first radiation image of multi-energy bands may be approximated as a model based on equation 3 below, $$I_{tr}(E) = I_{init}(E)e^{-\mu_f t_f - \mu_g t_g} \qquad \text{[Equation 3]}$$

where, $I_{tr}(E)$ corresponds with an intensity of X-rays that pass through an object being photographed, $I_{init}(E)$ corresponds with an intensity of X-rays that do not pass through the object being photographed, $\mu_f$ corresponds with an attenuation coefficient of an adipose tissue, $t_f$ corresponds with a thickness of the adipose tissue, $\mu_g$ corresponds with an attenuation coefficient of a glandular tissue, and $t_g$ corresponds with a thickness of the glandular tissue. Based on equation 3 above, the breast tissue being the object photographed includes a combination of the adipose tissue and the glandular tissue.

Since the attenuation coefficients $\mu_f$ and $\mu_f$ are well known in equation 3, unknown quantities include $t_f$ and $t_g$. Thus, if an X-ray image of different tube voltages, such as the first radiation image of multi-energy bands, is photographed, a thickness of each tissue may be obtained.

In the example embodiment, radiation images of two energy bands, such as, for example, a high energy band and a low energy band, may be used. It is understood that the implementations are not limited to the two energy bands, and radiation images of a different number may be used, for example, three or more energy bands may be used.

Calibration may be performed for radiation images of multi-energy bands by using a wedge phantom having a stepped or triangular shape. Calibration may be performed to estimate a functional relation between a thickness of a local region of a human body and a phantom by mapping radiation images of the local region of the human body and the phantom. The functional relation obtained by performing the calibration may be used to obtain a tissue ratio and tissue thickness of the local region from radiation images of multi-energy bands.

Figure 2:
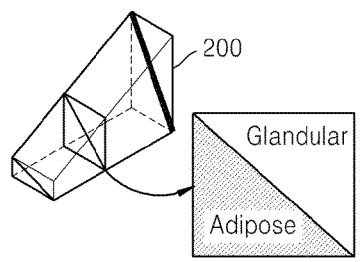
FIG. 2 illustrates a thickness variable phantom, based on an example embodiment.

FIG. 2 illustrates a thickness variable phantom 200, based on an example embodiment.

Main tissue of breast tissue may include adipose tissue and glandular tissue. Densities of the adipose tissue and the glandular tissue may differ based on individuals. Thus, a phantom model having a variable thickness may be needed to reflect density changes.

In the example embodiment, the thickness variable phantom 200 used may include two tissues, the adipose tissue and the glandular tissue, having a variable thickness, like the breast tissue. Thus, a tissue ratio and tissue thickness of a local region of a human body may be estimated from a sheet of a radiation image of the thickness variable phantom 200 without capturing a phantom image of all densities. However, the example embodiment is not limited to the thickness variable phantom 200, and It is understood that the implementations are not limited to the thickness variable phantom 200, and a different type of phantom, for example, having a similar characteristic to that of the thickness variable phantom 200 may be used.

As described above, a normal tissue including the breast tissue of a human body may include the adipose tissue and the glandular tissue. However, the breast tissue may include an abnormal tissue such as, for example, a tissue mass. In this case, radiation images of multi-energy bands may include three tissue types 1) the adipose tissue, 2) the glandular tissue, and 3) the abnormal tissue such as the tissue mass.

If the radiation images of multi-energy bands include the abnormal tissue like the tissue mass, having different components from those of the two main tissues of the adipose tissue and the glandular tissue, a mapping distribution of the abnormal tissue obtained by mapping the radiation images of the breast tissue and the thickness variable phantom 200 may be different from the mapping distribution obtained by mapping the two main tissues of the adipose tissue and the glandular tissue due to an influence of an attenuation coefficient of the abnormal tissue. Therefore, in the example embodiment, a method of enhancing and expressing the abnormal tissue having a different mapping distribution from that of the two main tissues of the adipose tissue and the glandular tissue by identifying the abnormal tissue and the adipose tissue and the glandular tissue may be performed in relation to the attenuation coefficient of the abnormal tissue.

Referring to FIG. 1, the image mapping unit 110 may generate a mapping image in which first radiation images of multi-energy bands of the local region of the human body are mapped to a second radiation image of the thickness variable phantom 200. In this regard, the local region of the human body is the breast tissue as described above. For example, the first radiation images may be obtained by photographing the breast tissue, and the second radiation image may be obtained by photographing the thickness variable phantom 200.

For example, the image mapping unit 110 may map pixels of the same positions of the first radiation images to the second radiation image. Furthermore, the imaging mapping unit 110 may generate the mapping image by detecting a pixel of a redundant position of the second radiation image from a result of mapping the pixels of the same positions of the first radiation images to the second radiation image.

Figure 3:
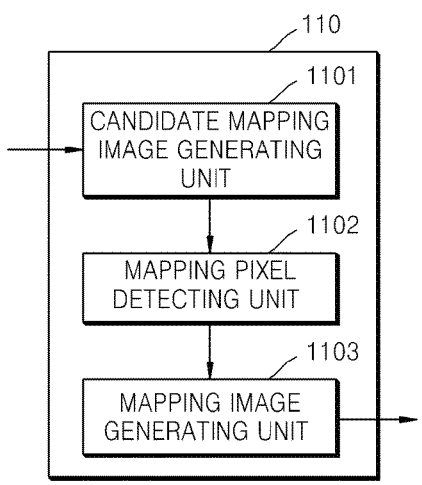
FIG. 3 is a block diagram illustrating an image mapping unit, based on an example embodiment.

FIG. 3 illustrates a block diagram of the image mapping unit 110, based on an example embodiment. Referring to FIG. 3, the image mapping unit 110 may include a candidate mapping image generating unit 1101, a mapping pixel detecting unit 1102, and a mapping image generating unit 1103.

Figure 4A:
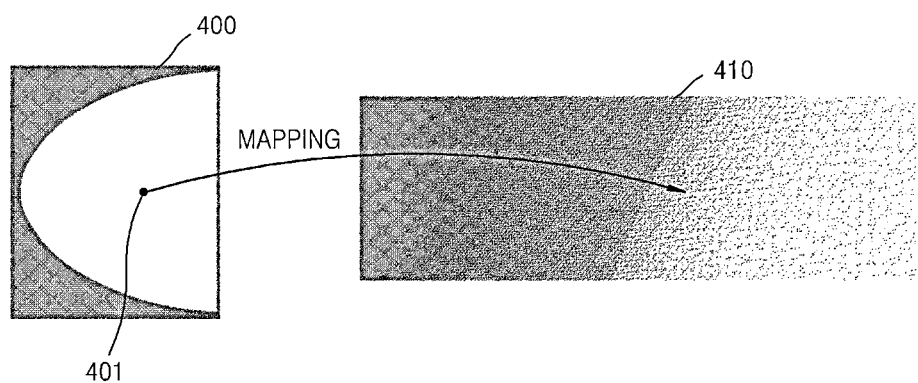
FIG. 4A illustrates an outline of an image mapping method, based on an example embodiment.

FIG. 4A illustrates an outline of an image mapping method, based on an example embodiment. Referring to FIG. 4A, a pixel 401 of a first radiation image 400 of breast tissue may be mapped to a second radiation image 410 of a thickness variable phantom. In this regard, such mapping may be performed based on an intensity of the pixel 401. The first radiation image 400 may be a radiation image of a high energy band or a radiation image of a low energy band.

Although the first radiation image 400 of FIG. 4A is only one image, the image mapping unit 110 may map the pixels 401 of the same positions of the radiation image of the high energy band and the radiation image of the low energy band to the second radiation image 410.

Referring to FIG. 3, the candidate mapping image generating unit 110 generates candidate mapping images corresponding to images obtained by mapping all pixels of the same positions of the first radiation images to the second radiation image. This will be described in more detail with reference to FIGS. 4B and 4C.

Figure 4B:
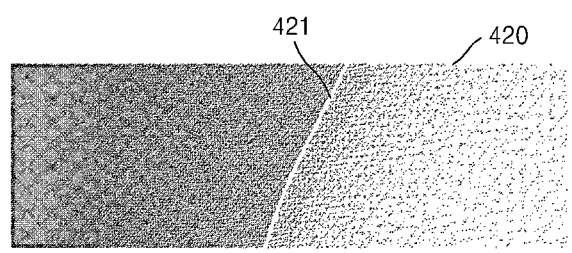
FIG. 4B is a diagram illustrating a candidate mapping image to which a radiation image of a low energy band is mapped, based on an example embodiment.
Figure 4C:
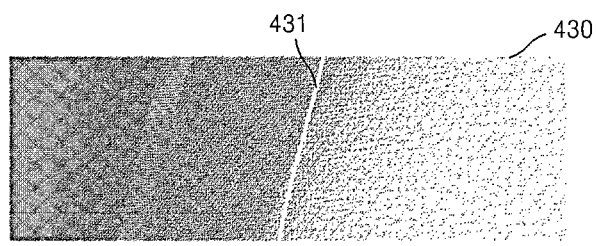
FIG. 4C is a diagram illustrating a candidate mapping image to which a radiation image of a high energy band is mapped, based on an example embodiment.

FIG. 4B illustrates a candidate mapping image 420 to which a radiation image of a low energy band may be mapped, based on an example embodiment. FIG. 4C illustrates a candidate mapping image 430 to which a radiation image of a high energy band is mapped, based on an example embodiment.

Referring to FIG. 4B, the candidate mapping image generating unit 1101 may map a pixel of the radiation image of the low energy band to a second radiation image, and may generate the candidate mapping image 420 in which a mapping result line 421 is indicated. Also, the candidate mapping image generating unit 1101 may map a pixel of the same position of the radiation image of the high energy band as the radiation image of the low energy band to the second ration image, and may generate the candidate mapping image 430 in which a mapping result line 431 is indicated.

The mapping result lines 421 and 431 may be obtained by mapping a thickness of the breast tissue in pixels of the radiation images of the high energy band and the low energy band to the thickness variable phantom. The thickness of the breast tissue indicates a thickness of the breast tissue compressed due to a mammography procedure.

In this regard, the mapping result lines 421 and 431 may have different inclinations since pixels of the same positions of the breast tissue are obtained through radiation of different energy bands having different attenuation coefficients. In other words, the pixels of the same positions may have different intensities.

Referring to FIG. 3, the candidate mapping image generating unit 1101 may generate candidate mapping images, such as, for example, the candidate mapping images 420 and 430 of FIGS. 4A and 4B, respectively.

The mapping pixel detecting unit 1102 may combine corresponding candidate mapping images and may detect a pixel mapped to a redundant position of the corresponding candidate mapping images. The corresponding candidate mapping images may be candidate mapping images of pixels of the same positions, such as the candidate mapping images 420 and 430. The mapping pixel detecting unit 1102 will now be described in more detail with reference to FIG. 4D.

Figure 4D:
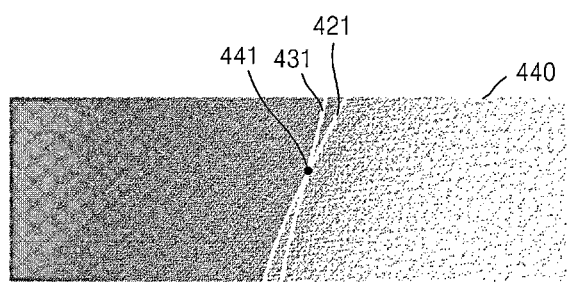
FIG. 4D is a diagram illustrating detection of a pixel mapped to a redundant position in a mapping pixel detection unit, based on an example embodiment.

FIG. 4D illustrates a diagram for explaining detection of a pixel 441 mapped to a redundant position in the mapping pixel detection unit 1102, based on an example embodiment. Referring to FIG. 4D, a combination image 440 is a combination of the candidate mapping images 420 and 430 of FIGS. 4A and 4B, respectively. The mapping pixel detecting unit 1102 may combine the corresponding candidate mapping images generated by the candidate mapping image generating unit 1101.

The combination image 440 may include the mapping result lines 421 and 431 indicated in the candidate mapping images 420 and 430 of FIGS. 4A and 4B, respectively. The mapping result lines 421 and 431 are obtained by mapping a thickness of the breast tissue in pixels of the radiation images of the high energy band and the low energy band to the thickness variable phantom, as described above.

In equation 3, the radiation image of the high energy band and the radiation image of the low energy band may be used to estimate the thickness of the breast tissue. Since values of the thickness may be represented by variables $t_f$ and $t_g$ in Equation 3, two simultaneous equations may be needed to obtain the values of the thickness that are represented by variables $t_f$ and $t_g$.

Referring to FIG. 4D, the two simultaneous equations correspond to the mapping result lines 421 and 431 that are mapped from the radiation images of different energy bands. Therefore, the pixel 441 of a position where the mapping result lines 421 and 431 of the combination image 440 cross each other or are redundant may correspond to an actual thickness of the breast tissue. For example, a thickness of a point of a thickness variable phantom corresponding to the pixel 441 may be the actual thickness of the breast tissue.

The mapping pixel detecting unit 1102 may detect the pixel 441 mapped to the redundant position from the combination image 440 that is a combination of the corresponding candidate mapping images.

The pixel 441 may be mapped to a pixel of a first radiation image. The candidate mapping image generating unit 1101 and the mapping pixel detecting unit 1102 generate and combine candidate mapping images of all pixels of the first radiation image, and may detect pixels of redundant positions like the pixel 441 from a combination image.

Referring to FIG. 3, the mapping image generating unit 1103 may indicate the pixels of the redundant positions in a second radiation image and may generate a mapping image. The mapping image generating unit 1103 may indicate mapping pixels corresponding to all pixels of the first radiation image and the second radiation image and may generate the mapping image.

Figure 5:
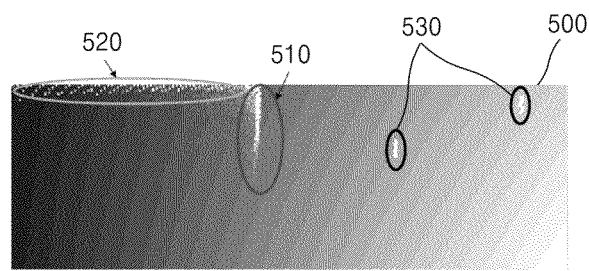
FIG. 5 is a diagram illustrating a mapping image generated by a mapping image generating unit, based on an example embodiment.

FIG. 5 illustrates a mapping image 500 generated by the mapping image generating unit 1103, based on an example embodiment. Referring to FIG. 5, the mapping image 500 may be an image finally generated by the image mapping unit 110. The mapping image 500 may include results obtained by mapping all pixels of first radiation images. As described above, since the breast tissue may include mostly normal tissues, the mapping image 500 may include a reference region 510 including most of mapping pixels. If the breast tissue includes abnormal tissue, the mapping image 500 includes at least one peculiar region 530. The reference region 510 and the peculiar region 530 will be described in more detail later.

For reference, when the breast tissue is photographed, a region 520 may indicate the breast tissue that is not compressed. In the example embodiment, the reference region 510, which indicates the breast tissue may be compressed, is used.

Referring back to FIG. 1, the image analyzing unit 120 may analyze 1) the reference region 510 corresponding to the normal tissue of the local region and 2) the peculiar region 530 corresponding to the abnormal tissue of the local region based on the mapping image 500.

Figure 6:
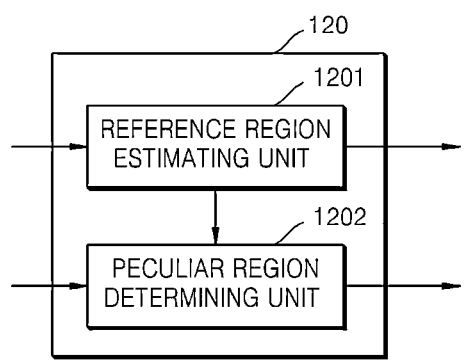
FIG. 6 is a block diagram illustrating an image analyzing unit, based on an example embodiment.

FIG. 6 illustrates the image analyzing unit 120, based on an example embodiment. Referring to FIG. 6, the image analyzing unit 120 may include a reference region estimating unit 1201 and a peculiar region determining unit 1202.

In a mapping image, a position in a reference region may indicate a thickness of normal breast tissue, and a position in a peculiar region may indicate a thickness of abnormal breast tissue. The reference region and the peculiar region have different positions since a density and an attenuation coefficient of the normal breast tissue may be different from those of the abnormal breast tissue. The position of the reference region may correspond to a value, the same as an entire thickness of the breast tissue, whereas the position of the peculiar region corresponds to a value, different from a thickness of the normal breast tissue.

The reference region estimating unit 1201 may estimate the position in the reference region in the mapping image. There are many methods of estimating the position in the reference region. Some of the many methods will be described in the example embodiment.

The reference region estimating unit 1201 may estimate the reference region based on a distribution of pixels mapped to the mapping image. For example, referring to FIG. 5, the reference region estimating unit 1201 may estimate a region based on a distribution of mapping pixels in the mapping image 500 as the reference region 510. For example, the distribution may be a region including the most mapping pixels. In this regard, the thickness of the normal tissue indicating the reference region may be estimated corresponding to a greatest pixel of each row of the reference region.

As another method, the reference region estimating unit 1201 may estimate the reference region by applying principal component analysis (PCA) or independent component analysis (ICA) to intensities of the pixels mapped to the mapping image.

The peculiar region determining unit 1202 may determine at least one peculiar region separate from the reference region in the mapping image. For example, the peculiar region determining unit 1202 determines a mapped pixel away from the reference region that is a distance greater than a threshold in the mapping image as a peculiar region. The threshold may be a value arbitrarily set based on a user's environment.

For example, referring to FIG. 5, the peculiar region determining unit 1202 may determine a region including mapping pixels separate from the reference region 510 in the mapping image 500 as the peculiar region 530.

In the example embodiment, a region separate from the reference region in the mapping image may be determined as the peculiar region since the abnormal tissue is mapped in a different position from the normal tissue in the mapping image due to a difference of a density and an attenuation coefficient as described above. Therefore, such a determination of the peculiar region may enable determination of a pixel of the first radiation image mapped to a pixel of the peculiar region, and furthermore a position of the abnormal tissue of the first radiation image.

Referring to FIG. 1, the enhancement image generation unit 130 may generate a tissue enhancement image that has a shape of the local region of the first radiation image and enhances the pixel positions, that correspond to the peculiar region, of the first radiation image.

An intensity of each pixel of the tissue enhancement image may be determined based on whether each pixel of the first radiation image is mapped to the reference region or the peculiar region.

For example, the enhancement image generation unit 130 may enhance the abnormal tissue by 1) reducing an intensity of a pixel of the first radiation image mapped to the reference region and 2) increasing an intensity of a pixel of the first radiation image mapped to the peculiar region in the tissue enhancement image.

Figure 7:
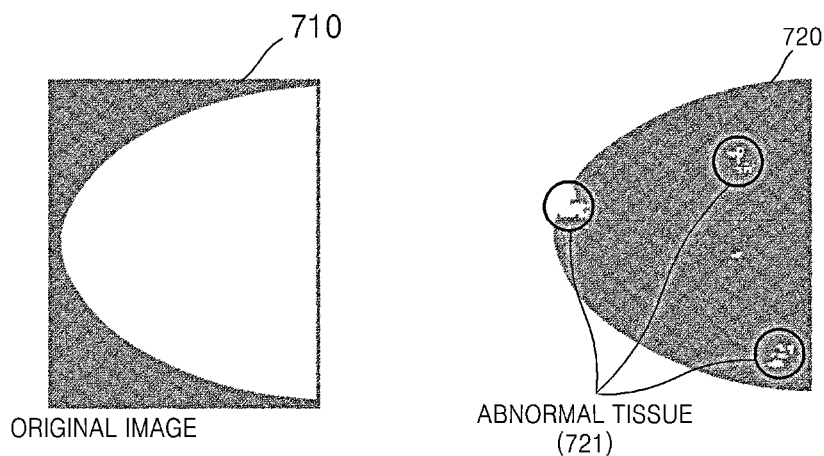
FIG. 7 is a diagram illustrating a tissue enhancement image, based on an example embodiment.

FIG. 7 illustrates a tissue enhancement image 720, based on an example embodiment. Referring to FIG. 7, the enhancement image generation unit 130 may generate the tissue enhancement image 720. A shape of the tissue enhancement image 720 may represent a tissue of a breast tissue of a first radiation image 710. Most pixels of the tissue enhancement image 720 may be mapped to a reference region, may have low intensities, and may indicate normal tissues. However, pixels 721 that may be mapped to a peculiar region of the tissue enhancement image 720 may be enhanced as having high intensities, and may indicate abnormal tissues.

In the example embodiment, the image processing apparatus 10 may generate the tissue enhancement image 720 through the image processing method described above, thereby more precisely providing a subject and a medical expert with diagnosis information regarding abnormal breast tissue. For example, the image processing apparatus 10 may generate the tissue enhancement image 720 in which anatomic structures of tissues of human organs are distinguished by using different absorption characteristics of the tissues for energy bands.

The image processing apparatus 10 may further include a tissue characteristics estimating unit 140. The tissue characteristics estimating unit 140 may estimate a thickness and density of a local region based on a shape and position of the analyzed reference region in a mapping image, and may determine an abnormal tissue type based on a shape and a position of the analyzed peculiar region.

For example, the tissue characteristics estimating unit 140 may estimate a component ratio and density of an adipose tissue or a glandular tissue based on the shape and position of the reference region analyzed in the mapping image. If an abnormal tissue has a relatively large size, the tissue characteristics estimating unit 140 may determine a type of a material of the abnormal tissue based on the position of the peculiar region. For example, if the peculiar region is far away from the reference region, the tissue characteristics estimating unit 140 may determine the abnormal tissue as a microcalcification tissue.

Figure 8:
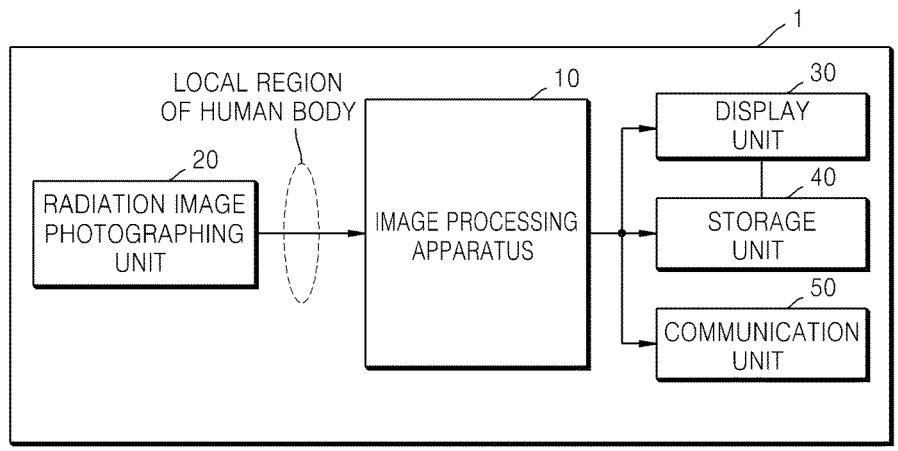
FIG. 8 is a block diagram illustrating a medical image system, based on an example embodiment.

FIG. 8 illustrates a medical image system 1, based on an example embodiment. Referring to FIG. 1, the medical image system 1 may include a radiation image photographing unit 20, the image processing apparatus 10, a display unit 30, a storage unit 40, and a communication unit 50. The image processing apparatus 10 of the example embodiment may be implemented by at least one processor.

The medical image system 1 of FIG. 8 may include the elements related to the example embodiment. Thus, it is understood that general-use elements may be further included in the medical image system 1 of FIG. 8.

The medical image system 1 of the example embodiment may include all image diagnosis systems that use, for example, X-rays. For example, the medical image system 1 may be a mammography image diagnosis system used to identify lesions in breast tissue including soft tissue, but not hard tissue such as bone, of a human body.

The radiation image photographing unit 20 may irradiate radiation onto a local region of the human body and a thickness variable phantom, and may obtain first radiation images of multi-energy bands of the local region of the human body and a second radiation image of the thickness variable phantom. The radiation image photographing unit 20 may irradiate radiation having a wideband spectrum onto the human body, and may obtain a plurality of radiation images reflecting an attenuation characteristic for each energy band by using a detector capable of identifying energy. The radiation image photographing unit 20 of the example embodiment may be used in mammography.

Furthermore, the radiation image photographing unit 20 may include a radiation generating unit (not shown) for irradiating radiation onto a subject and a detecting unit (not shown) for detecting a radiation image that passes through the human body. However, if the image processing apparatus 10 performs a detection function, the radiation image photographing unit 20 may include only the radiation generating unit (not shown) for irradiating radiation onto the subject.

The image processing apparatus 10 may generate a mapping image in which the first radiation images may be mapped to the second radiation image, may analyze a reference region corresponding to normal tissue of the local region and a peculiar region corresponding to abnormal tissue of the location region based on the mapping image, and may generate a tissue enhancement image that enhances regions of pixel positions of the first radiation images and may be mapped to the peculiar region having a shape of the local region in the first radiation images.

The image processing apparatus 10 of FIG. 8 may correspond to the image processing apparatus 10 of FIG. 1. The description of the image processing apparatus 10 of FIG. 1 may apply to that of the image processing apparatus 10 of FIG. 8, and thus a description of the image processing apparatus 10 of FIG. 8 will not be repeated here.

The display unit 30 may display the tissue enhancement image generated by the image processing apparatus 10. For example, the display unit 30 may include output devices, such as a display panel, a touch screen, a monitor, etc. and software modules for driving the output devices.

Therefore, a user of the medical image system 1 may view the tissue enhancement image in which the abnormal tissue is enhanced.

The storage unit 40 may store the tissue enhancement image generated by the image processing apparatus 10. For example, the storage unit 40 is a general storage medium and it is understood that the storage unit 40 may include a hard disk drive (HDD), a read only memory (ROM), a random access memory (RAM), a flash memory, and a memory card. Further, the storage unit 40 may store results obtained by the image processing apparatus 10.

The communication unit 50 may transmit the tissue enhancement image generated by the image processing apparatus 10 to an external device and may receive data from the external device. In this regard, the external device may be a remotely positioned medical image system, a general-purpose computer system, a facsimile, etc.

The communication unit 50 may communicate the data with the external device over any of a wired and wireless networks. Although the wired and wireless networks may include the Internet, a local area network (LAN), a wireless LAN, a wide area network (WAN), a personal area network (PAN), etc., the network is not limited to the wired and wireless networks, and the wired and wireless networks may be different types of networks that communicate information.

Also, it is understood that the storage unit 40 and the communication unit 50 may further have functions of reading and searching an image and be integrally formed as a picture archiving communication system (PACS).

Therefore, the medical image system 1 may display the tissue enhancement image 720 generated by processing radiation images, thereby providing a subject and a medical expert with diagnosis information regarding abnormal breast tissue. For example, the medical image system 1 may generate the tissue enhancement image 720 in which anatomic structures of tissues of human organs are distinguished by using different absorption characteristics of the tissues for energy bands.

Figure 9:
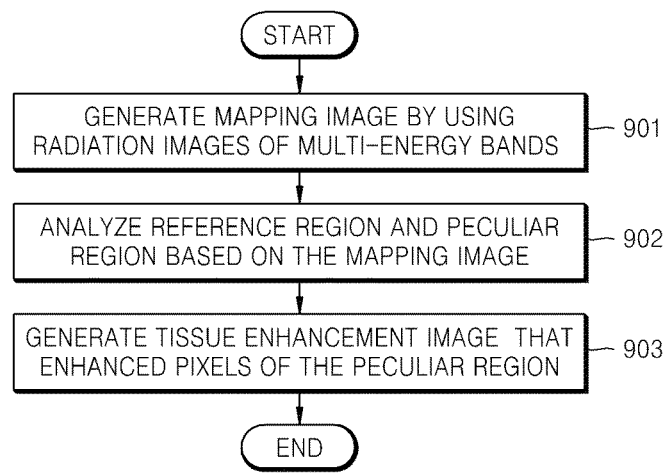
FIG. 9 is a flowchart illustrating an image processing method, based on an example embodiment.

FIG. 9 illustrates an image processing method, based on an example embodiment. The image processing method of the example embodiment may include operations time-serially processed by the image processing apparatus 10 of FIGS. 1 and 8. Although not described, the description of the image processing apparatus 10 may apply to that of the image processing method of the example embodiment.

In operation 901, the image mapping unit 110 may generate a mapping image in which first radiation images of multi-energy bands with respect to a local region of the human body are mapped to a second radiation image with respect to a thickness variable phantom.

In operation 902, the image analyzing unit 120 may analyze a reference region corresponding to normal tissue in the local region and a peculiar region corresponding to abnormal tissue in the local region based on the mapping image.

In operation 903, the enhancement image generating unit 130 may generate a tissue enhancement image that has a shape of the local region in the first radiation images and enhances regions of pixel positions, that are mapped to the peculiar region, of the first radiation images.

FIG. 10 illustrates an operation of FIG. 9 for generating a mapping image.

Referring to FIG. 10, in operation 1002, the candidate mapping image generating unit 1101 may map pixels of the same positions of the first radiation images to the second radiation image, and may generate corresponding candidate mapping images.

In operation 1002, the mapping pixel detecting unit 1102 may combine the corresponding candidate mapping images and may detect pixels mapped to redundant positions.

In operation 1003, the mapping image generating unit 1103 may display the pixels mapped to the redundant positions on the second radiation image and may generate a mapping image.

As described above, a diagnostic image in which an abnormal tissue is enhanced may be obtained. Thus, medical experts may determine whether a subject has a lesion, a size of the lesion, a position of the lesion, etc.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An image processing apparatus comprising:
    an image mapping unit for generating a mapping image in which first radiation images of multi-energy bands with respect to a local region of a body are mapped to a second radiation image with respect to a thickness variable phantom;
    an image analyzing unit for analyzing a reference region corresponding to normal tissue in the local region and a peculiar region corresponding to abnormal tissue in the local region based on the mapping image; and
    an enhancement image generating unit for generating a tissue enhancement image that has a shape of the local region in the first radiation images and enhances regions of pixel positions, that are mapped to the peculiar region, of the first radiation images.

2. The image processing apparatus of claim 1, wherein the image mapping unit maps pixels of the same positions of the first radiation images to the second radiation image.

3. The image processing apparatus of claim 2, wherein the image mapping unit generates the mapping image by detecting pixels mapped to redundant positions of the second radiation image from a result obtained by mapping the pixels of the same positions of the first radiation images to the second radiation image.

4. The image processing apparatus of claim 1, wherein the image mapping unit comprises:
    a candidate mapping image generating unit for mapping pixels of the same positions of the first radiation images to the second radiation image, and generating corresponding candidate mapping images;
    a mapping pixel detecting unit for combining the corresponding candidate mapping images and detecting pixels mapped to redundant positions; and
    a mapping image generating unit for displaying the pixels mapped to the redundant positions on the second radiation image and generating a mapping image.

5. The image processing apparatus of claim 1, wherein a position of the reference region of the mapping image indicates a thickness of the normal tissue, and a position of the peculiar region thereof indicates a thickness of the local region including the abnormal tissue.

6. The image processing apparatus of claim 1, wherein the image analyzing unit comprises:
    a reference region estimating unit for estimating the position of the reference region in the mapping image; and
    a peculiar region determining unit for determining at least one peculiar region separate from the reference region in the mapping image.

7. The image processing apparatus of claim 6, wherein the peculiar region determining unit determines a mapped pixel separate from the reference region by a distance that is greater than a threshold in the mapping image as the at least one peculiar region.

8. The image processing apparatus of claim 6, wherein the reference region estimating unit estimates the reference region based on a distribution of pixels mapped to the mapping image.

9. The image processing apparatus of claim 1, further comprising: a tissue characteristics estimating unit for estimating a thickness and density of a local region based on a shape and position of the analyzed reference region in the mapping image, and identifying an abnormal tissue type based on a shape and a position of the analyzed peculiar region.

10. The image processing apparatus of claim 1, wherein the first radiation images include one first radiation image from a first energy band of the multi-energy bands and another first radiation image from a second energy band of the multi-energy bands, the first energy band having a different energy than the second energy band.

11. An image processing method comprising:
    generating a mapping image in which first radiation images of multi-energy bands with respect to a local region of a body are mapped to a second radiation image with respect to a thickness variable phantom;
    analyzing a reference region corresponding to normal tissue in the local region and a peculiar region corresponding to abnormal tissue in the local region based on the mapping image; and
    generating a tissue enhancement image that has a shape of the local region in the first radiation images and enhances regions of pixel positions, that are mapped to the peculiar region, of the first radiation images.

12. The image processing method of claim 11, wherein the generating of the mapping image comprises: mapping pixels of the same positions of the first radiation images to the second radiation image.

13. The image processing method of claim 12, wherein the generating of the mapping image comprises: generating the mapping image by detecting pixels mapped to redundant positions of the second radiation image from a result obtained by mapping the pixels of the same positions of the first radiation images to the second radiation image.

14. The image processing method of claim 11, wherein the generating of the mapping image comprises:
- mapping pixels of the same positions of the first radiation images to the second radiation image, and generating corresponding candidate mapping images;
- combining the corresponding candidate mapping images and detecting pixels mapped to redundant positions; and
- displaying the pixels mapped to the redundant positions on the second radiation image and generating a mapping image.

15. The image processing method of claim 11, wherein the analyzing comprises:
- estimating the position of the reference region in the mapping image; and
- determining at least one peculiar region separate from the reference region in the mapping image.

16. The image processing method of claim 15, wherein the determining of the peculiar region comprises: determining a mapped pixel separate from the reference region by a distance that is greater than a threshold in the mapping image as the at least one peculiar region.

17. The image processing apparatus of claim 11, further comprising: estimating a thickness and density of a local region based on a shape and position of the analyzed reference region in the mapping image, and identifying a type of an abnormal tissue based on a shape and a position of the analyzed peculiar region.

18. A computer readable recording medium storing a program for executing a method of claim 11.

19. The image processing method of claim 11, wherein the first radiation images include one first radiation image from a first energy band of the multi-energy bands and another first radiation image from a second energy band of the multi-energy bands, the first energy band having a different energy than the second energy band.

20. A medical image system comprising:
- a radiation image photographing unit for irradiating radiation onto a local region of a body and a thickness variable phantom, and obtaining first radiation images of multi-energy bands of the local region of the body and a second radiation image of the thickness variable phantom;
- an image processing apparatus for generating a mapping image in which the first radiation images are mapped to the second radiation image, analyzing a reference region corresponding to normal tissue in the local region and a peculiar region corresponding to abnormal tissue in the local region based on the mapping image, and generating a tissue enhancement image that has a shape of the local region in the first radiation images and enhances regions of pixel positions, that are mapped to the peculiar region of the first radiation images; and
- a display unit for displaying the tissue enhancement image.

21. The medical image system of claim 20, wherein the image processing apparatus maps pixels of the same positions of the first radiation images to the second radiation image, detects pixels mapped to redundant positions of the second radiation image from a result obtained by mapping the pixels of the same positions of the first radiation images to the second radiation image, and generates the mapping image.

22. The medical image system of claim 20, wherein the image processing apparatus determines a mapped pixel separate from the reference region by a distance that is greater than a threshold in the mapping image as the at least one peculiar region.

23. The medical imaging system of claim 20, wherein the first radiation images include one first radiation image from a first energy band of the multi-energy bands and another first radiation image from a second energy band of the multi-energy bands, the first energy band having a different energy than the second energy band.

24. An image processing method comprising:
- generating a plurality of first radiation images corresponding to a plurality of energy bands with respect to a local region of a body and a second radiation image with respect to a thickness variable phantom;
- detecting a pixel of a redundant position based on the first radiation images and second radiation image; and
- enhancing regions of pixel positions, that are mapped to a peculiar region corresponding to abnormal tissue in the local region of the first radiation images based on the detecting operation.

25. The image processing method of claim 24, wherein the first radiation images include one first radiation image from a first energy band and another first radiation image from a second energy band, the first energy band having a different energy than the second energy band.

* * * * *